United States Patent [19]

Blakemore et al.

[11] 4,088,746

[45] May 9, 1978

[54] RADIOIMMUNOASSAY FOR THYROID-STIMULATING HORMONE (TSH)

[75] Inventors: Judith I. Blakemore, Mill Valley; Nathan Lewin, Corte Madera; Michael W. Burgett, Half Moon Bay, all of Calif.

[73] Assignee: Bio-Rad Laboratories, Inc., Richmond, Calif.

[21] Appl. No.: 742,391

[22] Filed: Nov. 11, 1976

[51] Int. Cl.$^2$ .................. A61K 43/00; G01N 33/16
[52] U.S. Cl. .................................... 424/1; 23/230 B; 23/230.6; 424/12
[58] Field of Search .................. 424/1, 1.5, 12; 23/230 B, 230.6

[56] References Cited

U.S. PATENT DOCUMENTS 3,853,987   12/1974   Dreyer .................................... 424/1
4,021,534   5/1977    Lafontaine ............................. 424/1

OTHER PUBLICATIONS

Koninckx et al, Acta Endocrinologica, vol. 81, No. 1, Jan., 1976, pp. 43-53.
Sluiter et al, Clinica Chimica Acta, vol. 42, Nov., 1972, pp. 255-262.

Primary Examiner—Benjamin R. Padgett
Assistant Examiner—Christine M. Nucker
Attorney, Agent, or Firm—Townsend and Townsend

[57] ABSTRACT

This invention provides a method for the radioimmunoassay of thyroid-stimulating hormone which utilizes a rapid and convenient version of a double antibody procedure. Highly purified second antibody is bound, by means of covalent bonds, to hydrolyzed polyacrylamide particles to produce a two-phase system. The solid phase comprises immobilized second antibody bound to the reaction product of labeled and unlabeled thyroid-stimulating hormone with the first antibody (first antibody-antigen complex) and the liquid phase comprises free (unbound) labeled and unlabeled thyroid-stimulating hormone. The two phases are separated and the radioactivity of either phase is measured.

10 Claims, 2 Drawing Figures

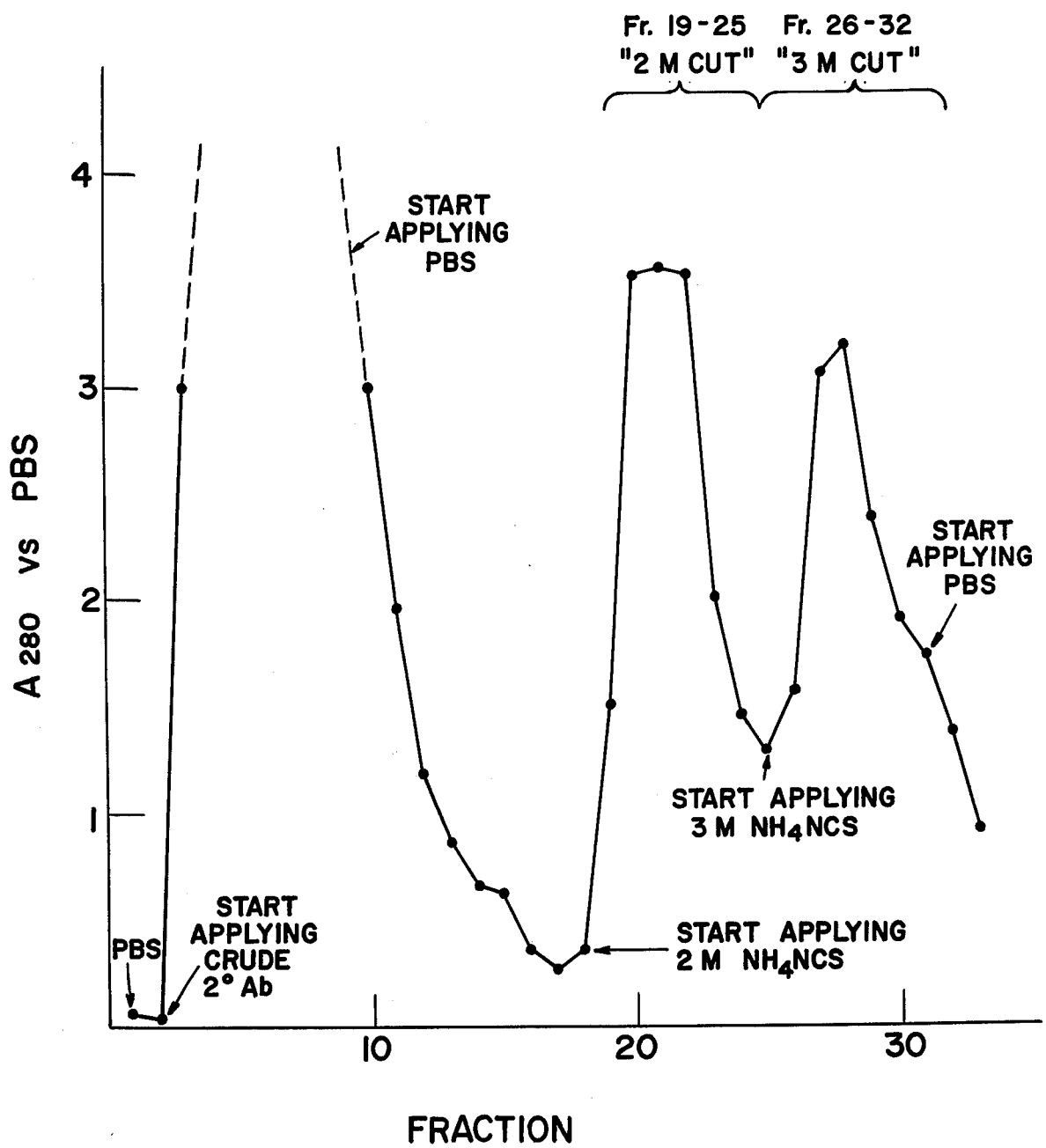
FIG _ 1

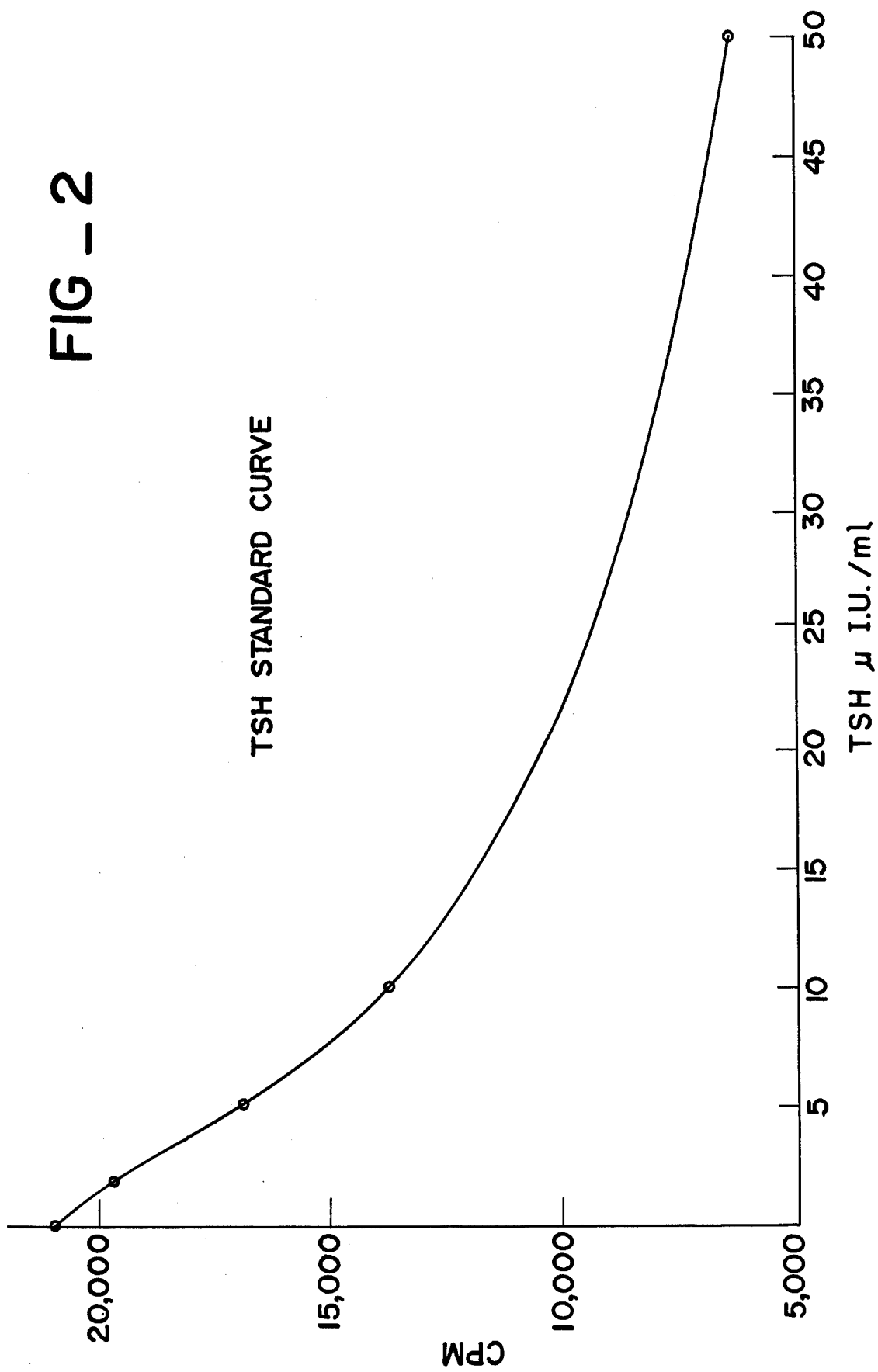
FIG_2
TSH STANDARD CURVE

RADIOIMMUNOASSAY FOR THYROID-STIMULATING HORMONE (TSH)

BACKGROUND OF THE INVENTION

1. Field of the Invention

This invention relates to a method for the radioimmunoassay of thyroid-stimulating hormone.

2. Description of the Prior Art

Double antibody radioimmunoassay principles are described by Kirkham and Hunter[1]. In general, these assays involve the use of a second antibody (anti-first antibody) to precipitate the first antibody-antigen complex. This method relies on the fact that the antigenic sites of the first antibody are distinct from the sites involved in the antibody activity of the molecule. In the specific case of a thyroid-stimulating hormone (TSH) assay, antibodies against TSH produced in rabbits (rabbit anti-human TSH) are first incubated with the TSH present in the aqueous sample to be determined and then with radioactively labeled TSH, so that some labeled and unlabeled TSH becomes bound, on a competitive basis, to the antibody molecules, while the remainder of unlabeled and labeled TSH remains free in solution. Second antibody (antibody against rabbit antibody molecules produced in goats) is then added, and it becomes bound to the first antibody-antigen complex. When the proportions of second antibody and first antibody are correct, a lattice of first antibody and second antibody molecules will form, resulting in a precipitate. The sample can be treated so as to effect a separation of bound labeled and unlabeled TSH from free labeled and unlabeled TSH, and the radioactivity of the bound TSH is measured. The amount of radioactivity bound is a function of the amount of unlabeled TSH present in the sample. Double antibody procedures to separate bound TSH from free hormone are available commercially. Beckman, in its radioimmunoassay for human thyroid-stimulating hormone makes use of the routine double antibody procedure to determine TSH. The procedure involves the addition of a carefully calibrated amount of a second antibody solution to form a precipitate comprising first antibody-antigen complex bound to the second antibody.

[1]Kirkham, E. E. and Hunter, W. M., Editors, Radioimmunoassay Methods (Edinburgh, Scotland: Churchill Livingstone, 1973).

Sorin has made commercially available a solid-phase second antibody radioimmunoassay for TSH in which the second antibody is coupled to cellulose. In the Sorin assay the sample containing the TSH to be determined is mixed with radioactively labeled TSH and the first antibody at room temperature for 18–24 hours. The solid phase second antibody is then added and incubated for 3 hours with agitation. The solid phase is separated, washed two times and the radioactivity in the solid phase is measured. A radioimmunoassay for TSH which utilizes the double antibody procedure wherein the second antibody is coupled to cellulose, is also described by W. J. Sluiter et al. in *Clin. Clim. Acta.*, 42 (1972) 255–262.

U.S. Pat. No. 3,555,143 issued Jan. 12, 1971 to R.E.-.A.C. Axen, et al. teaches the use of a solid phase first antibody in radioimmunoassays for proteins and polypeptides. Pharmacia has applied this single antibody technique in its commercially offered radioimmunoassay for TSH. In this procedure, the first antibody is covalently bound to a polydextran. The sample to be determined and the solid-phase first antibody are incubated at room temperature for 18–24 hours followed by addition of radioactively labeled TSH and further incubation with agitation for 18–24 hours. The solid phase is separated, washed three times and its radioactivity measured.

The patent application by Monthony et al. Ser. No. 621,197 filed Oct. 9, 1975 describes an immunofluorescent assay method in which the immune reactants are covalently bound to water insoluble hydrophilic polymeric particles of about 0.1–10 microns in size. The solid phase antibody is mixed with the antigen (or hapten) to be determined and corresponding antigen (or hapten) which has been fluorescently labeled, so as to bind a quantity of labeled and unlabeled antigen. The solid phase is separated and the fluorescence measured by optical spectroscopy, the concentration of the unknown immune reactant being a function of the value of the fluorescence.

The patent application by Wegfahrt et al., Ser. No. 718,308, filed Aug. 27, 1976 describes an improved radioimmunoassay for thyroid hormone utilizing a single antibody technique in which the antibody is covalently bound to hydrolyzed polyacrylamide particles as in Monthony et al. so as to separate bound thyroid hormone to be determined.

SUMMARY OF THE INVENTION

The present invention provides an improved double antibody radioimmunoassay for human thyroid stimulating hormone in which a highly purified second antibody is immobilized onto hydrophilic hydrolyzed polyacrylamide particles of a suspendable size to form a solid phase second antibody reagent. The immobilized second antibody reagent is used to precipitate the reaction product of the first antibody with labeled and unlabeled thyroid stimulating hormone (TSH-anti-TSH complex) so as to produce a two-phase system which permits for quick and efficient separation of bound TSH in the solid phase from free TSH in the liquid phase.

Important to the method is the selection of a polyacrylamide reagent in a particular size range of about 0.10 to 10 microns which provides a substantially stable suspension during incubation. Such polyacrylamide particles have such a low nonspecific adsorption through mechanical, ionic and/or hydrophobic interactions that in an assay situation the necessity of washing the insolubilized reagent prior to the determination of radioactivity bound to the solid phase is eliminated. This is in contrast to other solid phase radioimmunoassays for TSH which require two to three washes to lower the background radioactivity prior to the measurement of the radioactivity of the labeled TSH, e.g., Sorin and Pharmacia products.

The ability of the second antibody-polyacrylamide reagent to form a semi-stable suspension eliminates the necessity of continuous agitation of the sample tubes during incubation. The incubation steps can therefore be conveniently carried out at higher temperatures in any common laboratory water bath or heating block incubator. The use of increased incubation temperature significantly decreases the incubation time required in this method (5 hours) from that of other solid phase TSH radioimmunoassays (Sorin, 21–24 hours; Pharmacia, 36–48 hours).

The reduced incubation time noted above is also made possible through the use of highly purified second antibodies coupled to the polyacrylamide particles. As will be described hereinafter, antibody purification techniques are employed to separate and select out essentially those species of antibodies having relatively high affinity for the antigenic determinants on the first antibody. In addition, the solid phase second antibody permits the use of excess reagent to drive the reaction without encountering the problems of "post-zone" effects seen in conventional double antibody systems.

The novel highly purified second antibodies covalently bonded to polyacrylamide particles of this invention are analogously applicable to and useful as a reagent in immunoassays for various other antigenic entities in biological and other fluids. In general, this immobilized second antibody reagent may be similarly employed in any radioimmunoassay involving the use of first antibody produced in a first animal, the present second antibody from a second animal being highly specific for all such first antibodies whether or not the first antibody has been bound to its labeled or unlabeled antigen. For example, in the present preferred embodiment a first antibody to human TSH is produced in rabbits. A second antibody to this (rabbit anti-human TSH) first antibody is produced in goats. This same second antibody is specific to any antibody produced in rabbits. As an illustration it could be used in a double antibody radioimmunoassay for growth hormone in which rabbit antiserum against human growth hormone is used as the first antibody. The same procedures apply to antibodies produced in different pairs of animals.

Thus the present immobilized second antibody reagent may be used in a double antibody type radioimmunoassay for the following: steroid hormones, thyroid hormones, protein hormones, adrenal hormones, tumor and cancer associated proteins, therapeutic control drugs, drugs, of abuse, prostaglandins, nucleotides and nucleic acids, vitamins, antibiotics, and the like.

BRIEF DESCRIPTION OF THE DRAWINGS

FIG. 1 — Sample Elution Profile of Second Antibody; and

FIG. 2 — Sample Standard Curve, cpm versus concentration.

DESCRIPTION OF THE PREFERRED EMBODIMENT

The following is a description of a typical preparation of reagents. Other methods and raw materials may be used.

Preparation of Insolubilized Precipitating Antibody Reagent

The Insolubilized Precipitating Antibody reagent is prepared by coupling highly purified goat anti-rabbit gamma globulin to hydrolyzed polyacrylamide beads. Preparation of the microbead reagent can be divided into the following steps: (1) Purification of goat anti-rabbit gamma globulin; (2) Hydrolysis of polyacrylamide particles with sodium hydroxide; and (3) Coupling of purified second antibody to the hydrolyzed microbeads.

1. PURIFICATION OF GOAT ANTI-RABBIT GAMMA GLOBULIN

A. Titration of CM Bio-Gel A (One of a series of agarose gels offered by Bio-Rad Laboratories, Inc. of Richmond, California)

CM Bio-Gel A, 100–200 mesh, sodium form (250ml hydrated in 0.02% sodium azide in water) is converted to the acid form by washing with 1.5 liter of 0.1N HCl and washed exhaustively with the deionized water. The gel is then removed from the filter and resuspended in 500ml deionized water. 50ml of the suspension is then tested for pH and conductivity before and after adding aliquots of 0.1N NaOH. Before adding NaOH, the conductivity of the gel should be less than 25 μmhos. The micromoles of the acid per ml of gel are calculated from the equivalence point of the titration curve. At this point the hydroxide ions added are equivalent to the carboxylate ions on the gel.

B. Coupling Rabbit Gamma Globulin to Gel

The gel which has been converted to the acid form is slowly washed with dilute phosphate buffer (e.g., 0.001 to 0.01M), followed by suspension in the above buffer at a concentration of 0.5ml settled gel per ml of suspension (e.g., 400ml settled gel is suspended in buffer to 800ml). The pH is adjusted to 6.3 with 0.1N HCl and rabbit gamma globulin (15mg per ml of gel) and 1-ethyl-3-(3-dimethylaminopropyl) carbodiimide (EDAC, conveniently 1.5 equivalents per equivalent of acid groups on the gel) are added as solids. The suspension is stirred for one hour maintaining the pH at 5.5 to 6.5 and then is stirred overnight at room temperature.

C. Purification of Second Antibody on the Column

The immunosorbent gel prepared in the previous step is packed by gravity into a suitable chromatography column and washed with phosphate buffered saline (PBS) until the UV absorbance at 280nm of the eluted buffer is close to background. The column is then washed with one bed volume of 6M urea in PBS and then PBS again.

The second antibody (anti-rabbit gamma globulin, preferably goat anti-rabbit gamma globulin) is applied to the column at a flow rate of not more than 2ml per minute. The column is washed with PBS and the later serum colored fractions eluted from the column are tested for antibody activity, e.g., with double diffusion agarose plates. Low and high affinity antisera were empirically obtained by eluting the antisera with successively higher concentrations of a chaotropic agent (ammonium thiocyanate) using 1M ammonium thiocyanate, followed by 3M ammonium thiocyanate. The elution is monitored by reading the UV absorbance of the collected fractions. The fractions eluted with 3M thiocyanate are pooled and dialyzed against PBS. These fractions represent the high affinity antibodies which provide the short incubation periods of the present assay.

A sample elution profile is shown in FIG. 1 in which elutions were with 2M and 3M ammonium thiocyanate.

2. HYDROLYSIS OF POLYACRYLAMIDE BEADS

Bio-Rad P-6 polyacrylamide beads are hydrolyzed in 2N NaOH overnight at elevated temperatures, conveniently at 37°–40° C, to convert the amide groups to carboxylate ions and then washed exhaustively in deionized water, followed by dilute phosphate buffer. The hydrolyzed beads are resuspended in the buffer at a concentration of 10g per liter. The polyacrylamide beads are the same as those used in the above cited Monthony et al. and Wegfahrt et al. patent applications.

3. COUPLING OF SECOND ANTIBODY TO MICROBEADS

Hydrolyzed microbeads at a bead concentration of 5g per liter in dilute phosphate buffer and purified antibody at a concentration of 40–50mg per gram of beads (concentration of second antibody is determined using an extinction coefficient of 13.0 for a 1% solution at 280nm) are mixed together and the pH adjusted to 5.5 to 6.5 with HCl. The mixture is stirred 30 minutes at room temperature and EDAC is added at a concentration of 0.2g per gram of beads. The reaction mixture is stirred one hour at room temperature maintaining the pH at 5.5–6.5, and then stirred at 4° C overnight.

The coupled microbeads are purified by washing with PBS, 5M guanidine HCl in 0.05M phosphate buffer adjusted to pH 7, and PBS again. The buffers should be at 4° C prior to use. For each wash, at least 2 liters of solution is used per gram of beads. The beads are then suspended in PBS and allowed to stand for 3 hours at 4° C. The PBS is rinsed from the beads and the beads are washed with pH 8.4 barbital buffer (0.09M barbital, 0.005M EDTA, 0.01% sodium azide). The second antibody microbead reagent is then suspended in pH 8.4 barbital buffer containing salts and gelatin (0.09M barbital, 0.10M sodium chloride, 0.005M EDTA, 0.1% gelatin, and 0.01% sodium azide).

The second antibody-polyacrylamide bead reagent obtained was evaluated in the radioimmunoassay for human thyroid stimulating hormone. The preferred concentration of insolubilized precipitating antibody is an amount such that under the assay conditions, the precipitation of the TSH-first antibody complex is essentially complete. The amount used per assay tube is approximately 0.5–2.0mg, although other amounts can be used. The insolubilized precipitating antibody may be lyophilized from the buffer described above. The other reagents used in the assay are given below.

TRACER: $^{125}$I - Human Thyroid Stimulating Hormone

The tracer is conveniently human thyroid stimulating hormone which has been iodinated with the isotope $^{125}$I to a specific activity of 25 to 200 $\mu$Ci/$\mu$g, preferably 50 to 150 $\mu$Ci/$\mu$g. However, other specific activities may be used. The hormone may be iodinated by conventional methods described in the literature [see for example J. M. Burrin, Clin. Chim. Acta. 70 (1976) 153–159, and I. D. Goldfine et al., Endocrinology 95 (1974) 1228–1233]. The tracer is preferably but not essentially lyophilized from a solution containing buffered salts and gelatin. (e.g., pH 8.4 solution of 0.09M barbital buffer, 0.10M NaCl, 0.005M EDTA, 0.1% gelatin and 0.01% Sodium Azide.)

The amount of radioactive TSH added to each assay tube is generally chosen to give approximately 100,000 counts per minute when using a counter with approximately 80% efficiency. However, the assay may be run with smaller amounts (10,000 counts per minute) or larger amounts (200,000 counts per minute) of radioactivity added to each tube.

FIRST ANTIBODY

The first antibody is produced by injection of human TSH in rabbits, according to usual procedures. [See, for example, W. M. Odell and W. H. Daughaday (eds.) in *Principles Of Competitive Protein-Binding Assays* (Philadelphia: J. B. Lippincott Company, 1971).] It may be lyophilized from a pH 8.4 solution containing salts and gelatin of the concentration described for that of the tracer. The first antibody is diluted so that under the assay conditions in the absence of any added non-radioactive TSH, it binds 20–60% and preferably 30–45% of the radioactively labeled TSH (tracer).

STANDARDS

The standards contain human TSH in a protein-based solution which simulates human serum. The protein is preferably human serum albumin, although other animal proteins can be used; for instance, bovine serum albumin. The concentration is generally in the range of 3–12% by weight; conveniently 7% by weight. Preferably preservatives are added to the solution, for instance Sodium Azide at 0.01% by weight and disodium ethylenediaminetetraacetic acid dihydrate at 0.005M. The human TSH contained in the standards is obtained from commercial sources and the standards are calibrated against the international reference preparation of human TSH supplied by the World Health Organization (Medical Research Council, Holly Hill, London). Preferably, the standards are lyophilized from the pH 7 protein based solution. Standards are generally prepared containing 0, 2, 5, 10, 25 and 50 $\mu$I.U./ml TSH.

BUFFER

The buffer generally contains barbital and sodium barbital in the range of 0.025–0.10M, conveniently 0.09M. However, phosphate buffers have been found to be satisfactory. The pH of the buffer is generally in the range of 6.5–9.5, conveniently 8.2–8.6. Sodium chloride may be added to the buffer to make it more similar in ionic strength to serum, usually in a range of 0.05–0.16M. EDTA (disodium ethylenediaminetetraacetic acid dihydrate) is generally added to the buffer to prevent complement-mediated interferences with the antibody reactions. The EDTA concentration is usually in the range of 0.001–0.01M, and conveniently 0.005M. Gelatin may be added to the buffer to aid in preventing adsorption of the TSH to the reaction tube or to other substances. The amount of gelatin is conveniently 0.1% by weight. Sodium azide, at a concentration of 0.001–0.1%, conveniently 0.01%, may be used as a preservative. The preferred buffer formulation is 0.09M barbital, pH 8.4, containing 0.10M sodium chloride, 0.005M EDTA, 0.10% gelatin and 0.01% sodium azide. The buffer may be supplied as a lyophilized reagent.

BLANK

A solution containing buffer salts, gelatin and preservative is prepared and used in determination of non-specific binding of the $^{125}$I TSH reagent to the insolubilized precipitating antibody. This reagent contains 0.09M barbital buffer, pH 8.4, 0.10M Sodium Chloride, 0.005M Ethylenediaminetetraacetic acid, disodium salt, 0.1% gelatin, and 0.01% sodium azide as preservative. To this is added an appropriate amount of $^{125}$I TSH tracer and immobilized second antibody.

NORMAL CONTROL SERUM

A sample containing normal human serum which preferably has been lyophilized, may be included in the assay.

REACTION PARAMETERS

Reaction volumes are kept reasonably small, although larger volumes can be used and the concentrations adjusted accordingly. The incubation temperature is preferably in the range of 2°–50° C. If results are desired most rapidly, the assay tubes are conveniently incubated at elevated temperatures by heating above the ambient to 37° C for example. The reaction tubes may also be incubated at room temperature (approximately 25° C) or in the refrigerator (approximately 4° C). If preferred, the tubes may be incubated at different temperatures at the different steps in the assay.

The time necessary to allow each stage of the assay to progress to the desired completeness is dependent upon the incubation temperature. At 37° C, the incubation times are conveniently as specified in Example 1, although the time stage for each separate step may be varied by up to 3 hours and acceptable standard curves will still be obtained. At room temperature, an overnight incubation of primary antibody and standard is generally used, followed by addition of radioactively labeled TSH and a second overnight incubation, and lastly addition of second antibody and incubation for a short period of time (less than 4 hours). However, other time schemes may be used.

The sequence of additions of reagents in the assay may be varied; the preferred sequence is shown in Example 1.

EXAMPLE 1: USE OF A TYPICAL SET OF MATCHED REAGENTS

PREPARATION FOR ASSAY

Approximately 30 minutes before the assay is to be run:

1. Reconstitute $^{125}$I-human thyroid stimulating hormone, human thyroid stimulating hormone antiserum and insolubilized precipitating antiserum with 11.0ml distilled water.

2. Reconstitute zero standard and normal control serum with 5.0ml distilled water.

3. Reconstitute standards containing 2-50 μI.U./ml human thyroid stimulating hormone (Standards A through E) and buffer with 2.0ml distilled water.

4. Prepare a normal saline solution (0.9% or 0.154M NaCl) in distilled water. Store at room temperature.

Each reagent must be thoroughly dissolved and mixed with the added water before use. The insolubilized precipitating antibody reagent will be a fine suspension of polymeric bead particles and will appear cloudy. If more than 50 tubes are being run at one time two vials of $^{125}$I-TSH, antiserum to TSH and insolubilized precipitating antibody should be reconstituted. The contents of the two vials should be mixed in each case, prior to use in the assay.

ASSAY PROTOCOL

1. Label eighteen 12 × 75mm tubes in duplicate as follows: TC, Blank, Zero, A, B, C, D, E and NCS (Normal Control Serum). Label 2 tubes in duplicate for each patient serum sample.

2. Add 200μl buffer to the Blank tubes.

3. Add 200μl Zero Standard to the Blank and Zero tubes.

4. Add 200 μl standards A through E to the appropriate tubes.

5. Add 200μl normal control serum to the NCS tubes.

6. Add 200μl of each patient's serum to the appropriate tubes.

7. Add 200μl human TSH antiserum to all tubes except TC and Blank.

8. Mix tubes briefly by swirling or shaking test tube rack. Incubate all tubes (except TC) for 2 hours at 37° C.

9. Remove tubes from incubation. Add 200μl $^{125}$I-TSH to all tubes (including TC). Set TC tubes aside until step 12. Mix all other tubes briefly by shaking test tube rack. Incubate for 2 hours at 37° C.

10. Remove tubes from incubation. Add 200μl insolubilized precipitating antibody to all tubes (except TC). Mix and incubate for 1 hour at 37° C.

11. Remove tubes from incubation. Add 3.0ml saline to all tubes (except TC) and centrifuge for 10 minutes at 1,500 × G. Immediately after the centrifuge has stopped, decant tubes and blot the tube against filter paper or plastic-backed absorbent paper.

12. Count all tubes (including TC) for a length of time to give reasonable counting statistics for each tube. In general this will be one minute.

RESULTS

The concentrations of human thyroid stimulating hormone in control serum and the patient's samples are determined from a standard curve. Standard curves may be obtained by several methods, for example by plotting cpm vs. concentration or by plotting % bound/trace binding vs. concentration. FIG. 2 shows a sample standard curve where cpm is plotted vs. concentration. If this type of plot is used, it is recommended that the % trace binding and % blank be calculated as a check on the reliability of the assay. Percent blank may be determined by the formula:

$$\% \text{ Blank} = \frac{\text{average cpm for Blank tubes}}{\text{average cpm for TC tubes}} \times 100$$

The percent Blank should be less than 5%.

Percent trace binding may be calculated by the formula:

$$\% \text{ Trace binding} = \frac{\text{average cpm for Zero tubes}}{\text{average cpm for TC tubes}} \times 100$$

The percent trace binding should be greater than 20%. The standard curve must be constructed for each assay, as the actual numbers will be varied with the age of the reagents.

Sample data generated using this assay are shown below. These numbers were used to plot the standard curve in FIG. 2.

| Sample | cpm | Average cpm | % Bound/ Trace Binding | TSH Value |
|---|---|---|---|---|
| TC | 70299,70678 | 70489 | — | — |
| Blank | 1415, 1437 | 1426 | — | — |
| Zero | 20820,21296 | 21058 | 100% | 0μI.U./ml |
| A | 19743,19735 | 19739 | 93.7% | 2μI.U./ml |
| B | 16704,17056 | 16880 | 80.2% | 5μI.U./ml |
| C | 13739,13678 | 13709 | 65.1% | 10μI.U./ml |
| D | 9369, 9220 | 9295 | 44.1% | 25μI.U./ml |
| E | 6463, 6415 | 6439 | 30.6% | 50μI.U./ml |
| Control serum | 17631,17703 | 17667 | 83.9% | 4.2μI.U./ml |
| Patient 1 | 18465,18586 | 18526 | 88.0% | 3.3μI.U./ml |

%Blank $\frac{1426}{70489} \times 100 =$ 2.0% (should be less than 5%)

%Trace Binding $\frac{21058}{70489} \times 100 =$ 29.9% (should be greater than 20%)

What is claimed is:

1. An improved radioimmunoassay method for the determination of thyroid-stimulating hormone in biological and other fluids which comprises mixing together in an aqueous solution (a) the sample containing thyroid-stimulating hormone to be determined, (b) radioactively labeled thyroid-stimulating hormone and (c) antibodies against thyroid-stimulating hormone so as to competitively bind said labeled and unlabeled thyroid-stimulating hormone, thereafter adding polyacrylamide particles of about 0.1–10 microns in size having covalently bonded thereto a second antibody immunologically reactive with the said first antibody against thyroid stimulating hormone for reaction therewith to produce a two-phase system comprising a solid phase containing said bound portion of labeled and unlabeled thyroid-stimulating hormone and a liquid phase containing the unbound portion of labeled and unlabeled thyroid-stimulating hormone, separating the two phases from each other and measuring the radioactivity of either phase, the value of said radioactivity being a function of the concentration of said thyroid-stimulating hormone in the aqueous sample.

2. An improved radioimmunoassay method for the determination of thyroid-stimulating hormone in accordance with claim 1, wherein said two-phases are separated from each other and said solid phase is directly measured for radioactivity in the absence of washing.

3. An improved radioimmunoassay method for the determination of thyroid-stimulating hormone in accordance with claim 1, wherein said second antibody is highly purified and consists essentially of those species of antibodies having relatively high affinity for antigenic determinants on the said first antibody against thyroid-stimulating hormone.

4. In a double antibody radioimmunoassay for thyroid-stimulating hormone having a first antibody thyroid-stimulating hormone complex and a second antibody against said first antibody in which the second antibody is immobilized on solid phase particles, the improvement in which said solid phase particles are water insoluble hydrophilic polyacrylamide particles of about 0.1–10 microns in size for forming a substantially stable suspension during incubation, and wherein incubation can be executed at an elevated temperature of up to about 50° C substantially in the absence of agitation during the incubation.

5. The improved double antibody radioimmunoassay for thyroid-stimulating hormone in accordance with claim 4, wherein the incubation is executed at a temperature of about 37° C.

6. The improved double antibody radioimmunoassay for thyroid-stimulating hormone in accordance with claim 4, wherein said second antibody is highly purified and consists essentially of those species of antibodies having relatively high affinity for antigenic determinants on the said first antibody against thyroid-stimulating hormone.

7. A reagent useful in immunoassays employing first antibodies produced in a first animal comprising highly purified anti-first animal gamma globulin produced in a second animal covalently bonded to hydrophilic polyacrylamide particles of about 0.1–10 microns in size in hydrolyzed form.

8. A reagent in accordance with claim 7, wherein said highly purified gamma globulin antibodies consist essentially of those species having relatively high affinity for the antigenic determinants on said antibodies produced in said first animal.

9. A reagent in accordance with claim 8, wherein said first antibodies are produced in rabbits.

10. A reagent in accordance with claim 9, wherein said first antibodies are rabbit anti-human TSH.

* * * * *